US008877464B2

(12) United States Patent
Babiel et al.

(10) Patent No.: US 8,877,464 B2
(45) Date of Patent: Nov. 4, 2014

(54) QUALITATIVE AND QUANTITATIVE DETECTION OF MICROBIAL NUCLEIC ACIDS

(75) Inventors: Reiner Babiel, Seehausen (DE); Frank Bergmann, Iffeldorf (DE); Dorothea Johanna Sizmann, Iffeldorf (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 23 days.

(21) Appl. No.: 13/191,700

(22) Filed: Jul. 27, 2011

(65) Prior Publication Data

US 2012/0196283 A1 Aug. 2, 2012

Related U.S. Application Data

(60) Provisional application No. 61/368,983, filed on Jul. 29, 2010.

(51) Int. Cl.
*C12P 19/34* (2006.01)
*C12Q 1/68* (2006.01)
*G01N 21/64* (2006.01)

(52) U.S. Cl.
CPC .... *G01N 21/6428* (2013.01); *G01N 2021/6432* (2013.01); *G01N 2021/6441* (2013.01)
USPC .......................................... 435/91.2; 435/6.1

(58) Field of Classification Search
CPC .................. G01N 21/6824; G01N 2021/6432; G01N 2021/6441; C12Q 1/04; C12Q 1/06
USPC ...................................................... 435/91.2
See application file for complete search history.

(56) References Cited

U.S. PATENT DOCUMENTS

| | | | | |
|---|---|---|---|---|
| 5,476,774 | A * | 12/1995 | Wang et al. ................... | 435/91.2 |
| 5,789,153 | A | 8/1998 | Falkner et al. | |
| 2002/0192689 | A1 | 12/2002 | Pasloske et al. | |
| 2007/0148646 | A1 | 6/2007 | Laforest et al. | |
| 2010/0041040 | A1 | 2/2010 | Babiel et al. | |
| 2010/0129902 | A1 | 5/2010 | Schoenbrunner et al. | |

FOREIGN PATENT DOCUMENTS

| EP | 1131466 B1 | 7/2007 |
|---|---|---|
| EP | 10175527 | 11/2010 |
| WO | WO02/052030 | 7/2002 |

OTHER PUBLICATIONS

Sarrazin et al., Journal of Clincal Virology, vol. I 43, pp. 162-168, 2008.*
Bennett, Julie M., et al, 1999, "A quantitative PCR method for the assay of HIV-1 provirus load in peripheral blood mononuclear cells", Journal of Virological Methods, 83:11-20.
Gibson, Ursula E. M., et al., 1996, "A Novel Method for Real Time Quantitative RT-PCR", Genome Research, 6:995-1001.
Rho, Jae Kyun, et al., 2004, "Qualitative and Quantitative PCR Methods for Detection of Three Lines of Genetically Modified Potatoes", Journal of Agricultrual and Food Chemistry, 52:3269-3274.
Yang, Litao, et al., 2005, "Identification and Quantification of Three Genetically Modified Insect Resistant Cotton Lines Using Conventional and TaqMan Real-Time Polymerase Chain Reaction Methods", Journal of Agricultural and Food Chemistry, 53:6222-6229.
Huang, Jie, et al, 2008, "A Novel Real-Time Multiplex Reverse Transcriptase-Polymerase Chain Reaction for the Detection of HIV-1 RNA by Using Dual-Specific Armored RNA as Internal Control", Intervirology, 51:42-29.
Nash, Kevin A., et al., 1995, "Internal controls as performance monitors and quantitative standards in the detection by polymerase chain reaction of herpes simplex virus and cytomegalovirus in clinical specimens", Molecular and Cellular Probes, 9:347-356.
Roche, 2007, "COBAS TM AmpliPrep/COBAS TM TaqMan TM HIV-1 Test" XP007915387, pp. 1-36.
Roche Molecular Systems, 2009, "cobas TM TaqScreen MPX Test for use on the cobas s 201 system", XP20091124, pp. 1-60.
Yang, Litao, et al, 2005, "Identification and Quantification of Three Genetically Modified Insect Resistant Cotton Lines Using Conventional and TaqMan Real-Time Polymerase Chain Reaction", J. Agric. Food Chem., 53:6222-6229.
Desombere, I., et al., 2005, "Comparison of Qualitative (COBAS AMPLICOR HCV 2.0 versus VERSANT HCV RNA) and Quantitative (COBAS AMPLICOR HCV Monitor 2.0 versus Versant HCV RNA 3.0) Assays for Hepatitis C Virus (HCV) RNA Detection and Quantification: Impact on Diagnosis and Treatment of HCV Infections", Journal of Clinical Microbiology, 43:2590-2597.

* cited by examiner

*Primary Examiner* — Cynthia B Wilder
(74) *Attorney, Agent, or Firm* — Jeffery P. Bernhardt; Rhea C. Nersesian

(57) ABSTRACT

The present invention relates to new methods and uses for the qualitative and quantitative detection of microbial nucleic acids using at least a first control nucleic acid, or a first and a second control nucleic acid in different concentrations. The method is based on amplification of nucleic acids, for example the polymerase chain reaction. Further provided are kits comprising components for performing said methods and uses.

11 Claims, 4 Drawing Sheets

Expression vector of aRNA
particles and aRNA particles

QUALITATIVE AND QUANTITATIVE DETECTION OF MICROBIAL NUCLEIC ACIDS

CROSS REFERENCE TO RELATED APPLICATIONS

The present application claims the benefit of U.S. Provisional Application No. 61/368,983 filed on Jul. 29, 2010. The entire disclosure of the above-referenced prior application is hereby incorporated herein by reference in its entirety.

FIELD OF THE INVENTION

The present invention relates to new methods and uses for the qualitative and quantitative detection of microbial nucleic acids using at least a first control nucleic acid, or a first and a second control nucleic acid in different concentrations. The method is based on amplification of nucleic acids, for example the polymerase chain reaction. Further provided are kits comprising components for performing said methods and uses.

BACKGROUND OF THE INVENTION

In the field of molecular diagnostics, the detection and quantification of microbial nucleic acids using nucleic acid amplification reactions plays a significant role. The routine screening of blood donations for the presence of Hepatitis-C Virus (HCV), Human Immunodeficiency Virus (HIV), and/or Hepatitis-B Virus (HBV) is an example for the large-scale application of nucleic acid amplification and detection reactions. The latter comprise a variety of different techniques, the most commonly used one being the Polymerase Chain Reaction (PCR) introduced by Kary Mullis in 1984. Automated systems for PCR-based analysis often make use of real-time detection of product amplification during the PCR process. Key to such methods is the use of modified oligonucleotides carrying reporter groups or labels.

Qualitative detection of a microbial nucleic acid in a biological sample is crucial e.g. for recognizing an infection of an individual. Thereby, one important requirement for an assay for detection of a microbial infection is that false-negative or false-positive results be avoided, since such results would almost inevitably lead to severe consequences with regard to treatment of the respective patient. Thus, especially in PCR-based methods, a qualitative internal control nucleic acid is added to the detection mix. Said control is particularly important for confirming the validity of a test result: At least in the case of a negative result with regard to the microbial nucleic acid, the qualitative internal control reaction has to perform reactive within given settings, i.e. the qualitative internal control must be detected, otherwise the test itself is considered to be inoperative. However, in a qualitative setup, said qualitative internal control does not necessarily have to be detected in case of a positive result. For qualitative tests, it is especially important that the sensitivity of the reaction is guaranteed and therefore strictly controlled As a consequence, the concentration of the qualitative internal control must be relatively low so that even in a situation e.g. of slight inhibition the qualitative internal control is not be detected and therefore the test is invalidated.

On the other hand and in addition to mere detection of the presence or absence of a microbial nucleic acid in a sample, it is often important to determine the quantity of said nucleic acid. As an example, stage and severity of a viral disease may be assessed on the basis of the viral load. Further, monitoring of any therapy requires information on the quantity of a pathogen present in an individual in order to evaluate the therapy's success. For a quantitative assay, it is necessary to introduce a quantitative standard nucleic acid serving as a reference for determining the absolute quantity of a microbial nucleic acid. Quantitation can be effectuated either by referencing to an external calibration or by implementing an internal quantitative standard.

In the case of an external calibration, standard curves are created in separate reactions using known amounts of identical or comparable nucleic acids. The absolute quantity of a microbial nucleic acid is subsequently determined by comparison of the result obtained with the analyzed sample with said standard function. External calibration, however, has the disadvantage that a possible extraction procedure, its varied efficacy, and the possible and often not predictable presence of agents inhibiting the amplification and/or detection reaction are not reflected in the control.

This circumstance applies to any sample-related effects. Therefore, it might be the case that a sample is judged as negative due to an unsuccessful extraction procedure or other sample-based factors, whereas the microbial nucleic acid to be detected and quantified is actually present in the sample.

For these and other reasons, an internal quantitative standard added to the test reaction itself is of advantage. The internal quantitative standard has at least the following two functions in a quantitative test:

i) It monitors the validity of the reaction.
ii) It serves as reference in titer calculation thus compensating for effects of inhibition and controlling the preparation and amplification processes to allow a more accurate quantitation.

Therefore, in contrast to the qualitative internal control nucleic acid in a qualitative test which must be positive only in a target-negative reaction, the quantitative standard nucleic acid in a quantitative test has two functions: reaction control and reaction calibration. Therefore it must be positive and valid both in target-negative and target-positive reactions.

It further has to be suited to provide a reliable reference value for the calculation of high nucleic acid concentrations. Thus, the concentration of an internal quantitative standard nucleic acid needs to be relatively high.

The qualitative internal control nucleic acid and/or the internal quantitative standard nucleic acid can be competitive, non-competitive or partially competitive. A competitive qualitative internal control nucleic acid and/or internal quantitative standard nucleic acid carries essentially the same primer binding sites as the target and thus competes for the same primers as the target. Among the advantages of a competitive setup is, e.g., that fewer sets of different primers have to be introduced in the assay, thus reducing its costs and overall complexity. Furthermore, the functionality of the primers is monitored as are inhibition effects which are target primer-specific. A non-competitive qualitative internal control nucleic acid and/or internal quantitative standard nucleic acid has different primer binding sites than the target and thus binds to different primers. Advantages of such a setup comprise, among others, the fact that the single amplification events of the different nucleic acids in the reaction mixture can take place independently from each other without any competition effects. In a PCR using a partially competitive internal quantitative standard nucleic acid the respective control nucleic acid and at least one of the target nucleic acids compete for the same primers, while at least one other target nucleic acid binds to different primers.

Since the principles of a quantitative and a qualitative assay as described above display different requirements when compared to each other, also in view of regulatory requirements in various countries, the common approach used in the art has been the development of separate quantitative and qualitative assays for the same target nucleic acid, see e.g. Yang et al., J Agr Food Chem 2005, 53, 6222-6229.

The present invention provides an alternative solution displaying several advantages.

SUMMARY OF THE INVENTION

The present invention provides a method for simultaneously detecting and quantifying a microbial nucleic acid in a biological sample, the method comprising:
a) providing a reaction mixture comprising:
   a first control nucleic acid,
   one or more primer pairs that hybridize to distinct sequence portions of the microbial nucleic acid and to distinct sequence portions of the first control nucleic acid, and
   two or more probes that hybridize to each of the sequences amplified by the one or more primer pairs, wherein the microbial nucleic acid and the first control nucleic acid hybridize to different probes;
b) adding the biological sample to the reaction mixture;
c) performing one or more cycling steps, wherein each cycling step comprises:
   an amplifying step comprising producing one or more amplification products derived from the microbial nucleic acid if present in the sample and producing an amplification product derived from the first control nucleic acid, and
   a hybridizing step comprising hybridizing the amplification products with the two or more probes, wherein the two or more probes are each labeled with a donor fluorescent moiety and a corresponding acceptor fluorescent moiety and each of the two or more probes carries a different fluorescent moiety dye; and
d) detecting and measuring fluorescent signals generated in step c),
wherein the fluorescent signals generated by the first control nucleic acid and the microbial nucleic acid are proportional to their concentration and are indicative of the detection and quantification of the microbial nucleic acid, and wherein the fluorescent signals from the first control nucleic acid are indicative of an amplification occurring in the amplifying step even in the absence of the fluorescent signals from the microbial nucleic acid.

In some embodiments, the fluorescent signals from the first control nucleic acid are analyzed by different criteria to obtain a quantitative result and/or a qualitative result.

Additionally, the present invention provides a method for simultaneously detecting and quantifying a microbial nucleic acid in a biological sample, said method comprising:
a) providing a reaction mixture comprising:
   a first and a second control nucleic acid in different concentrations,
   one or more primer pairs that hybridize to distinct sequence portions of the microbial nucleic acid and to distinct sequence portions of the first and the second control nucleic acid, and
   three or more probes that hybridize to each of the sequences amplified by the one or more primer pairs, wherein the microbial nucleic acid and the first and second control nucleic acid each hybridize to different probes;
b) adding the biological sample to the reaction mixture;
c) performing one or more cycling steps, wherein each cycling step comprises:
   an amplifying step comprising producing one or more amplification products derived from the microbial nucleic acid if present in the sample and producing an amplification product derived from the first control nucleic acid and an amplification product derived from the second control nucleic acid, and
   a hybridizing step comprising hybridizing the amplification products with the three or more probes, wherein the three or more probes are each labeled with a donor fluorescent moiety and a corresponding acceptor fluorescent moiety and each of the three or more probes carries a different fluorescent moiety dye; and
d) detecting and measuring fluorescent signals generated in step c),
wherein the fluorescent signals generated by the first control nucleic acid and the microbial nucleic acid are proportional to their concentration and are indicative of the detection and quantification of the microbial nucleic acid, and wherein the fluorescent signals from the second control nucleic acid are indicative of an amplification occurring in the amplifying step even in the absence of the fluorescent signals from the microbial nucleic acid.

In some embodiments, the first control nucleic acid is a quantitative standard nucleic acid and the second control nucleic acid is a qualitative internal control nucleic acid. In other embodiments, the methods comprise in step d) determining the quantity of the microbial nucleic acid in the biological sample by comparison of the signals generated by the microbial nucleic acid and the first control nucleic acid. A further embodiment employs a polymerase enzyme having 5' to 3' exonuclease activity. In another embodiment of the invention, the first control nucleic acid is present in a concentration of 20-5000 times the limit of detection of the microbial nucleic acid, and the second control nucleic acid is present in a concentration of 1-25 times the limit of detection of the microbial nucleic acid. In another embodiment of the invention, the first and second control nucleic acids are provided within one control reagent.

Additionally the present invention provides kits for simultaneously detecting and quantifying a microbial nucleic acid in a biological sample comprising a first and a second control nucleic acid in different concentrations, one or more primer pairs that hybridize to distinct sequence portions of the microbial nucleic acid and to distinct sequence portions of the first and second control nucleic acid, and probes that hybridize to each of the sequences amplified by the one or more primer pairs, wherein the first and second control nucleic acids are provided within one control reagent.

The present invention further provides kits for simultaneously detecting and quantifying a microbial nucleic acid in a biological sample comprising a first and a second control nucleic acid in different concentrations, one or more primer pairs that hybridize to distinct sequence portions of the microbial nucleic acid and to distinct sequence portions of the first and second control nucleic acid, and probes that hybridize to each of the sequences amplified by the one or more primer pairs. In some embodiments, the first and second control nucleic acid are amplified by the same primer pair but hybridize to different probes.

Additionally the present invention provides an analytical system for simultaneously detecting and quantifying a microbial nucleic acid in a biological sample comprising a sample preparation module comprising a lysis buffer and a vessel for isolating and purifying the microbial nucleic acid, and an amplification and detection module comprising a reaction receptacle in which the methods performed comprise:
a) providing a reaction mixture comprising:
   a first control nucleic acid,
   one or more primer pairs that hybridize to distinct sequence portions of the microbial nucleic acid and to distinct sequence portions of the first control nucleic acid, and
   two or more probes that hybridize to each of the sequences amplified by the one or more primer pairs, wherein the microbial nucleic acid and the first control nucleic acid hybridize to different probes;
b) adding the biological sample to the reaction mixture;
c) performing one or more cycling steps, wherein each cycling step comprises:
   an amplifying step comprising producing one or more amplification products derived from the microbial nucleic acid if present in the sample and producing an amplification product derived from the first control nucleic acid, and
   a hybridizing step comprising hybridizing the amplification products with the two or more probes, wherein the two or more probes are each labeled with a donor fluorescent moiety and a corresponding acceptor fluorescent moiety and each of the two or more probes carries a different fluorescent moiety dye; and
d) detecting and measuring fluorescent signals generated in step c),
wherein the fluorescent signals generated by the first control nucleic acid and the microbial nucleic acid are proportional to their concentration and are indicative of the detection and quantification of the microbial nucleic acid, and wherein the fluorescent signals from the first control nucleic acid are indicative of an amplification occurring in the amplifying step even in the absence of the fluorescent signals from the microbial nucleic acid.

Further, the amplification and detection module of the invention can further comprise a reaction receptacle in which the methods performed comprise:
a) providing a reaction mixture comprising:
   a first and a second control nucleic acid in different concentrations,
   one or more primer pairs that hybridize to distinct sequence portions of the microbial nucleic acid and to distinct sequence portions of the first and the second control nucleic acid, and
   three or more probes that hybridize to each of the sequences amplified by the one or more primer pairs, wherein the microbial nucleic acid and the first and second control nucleic acid each hybridize to different probes;
b) adding the biological sample to the reaction mixture;
c) performing one or more cycling steps, wherein each cycling step comprises:
   an amplifying step comprising producing one or more amplification products derived from the microbial nucleic acid if present in the sample and producing an amplification product derived from the first control nucleic acid and an amplification product derived from the second control nucleic acid, and
   a hybridizing step comprising hybridizing the amplification products with the three or more probes, wherein the three or more probes are each labeled with a donor fluorescent moiety and a corresponding acceptor fluorescent moiety and each of the three or more probes carries a different fluorescent moiety dye; and
d) detecting and measuring fluorescent signals generated in step c),
wherein the fluorescent signals generated by the first control nucleic acid and the microbial nucleic acid are proportional to their concentration and are indicative of the detection and quantification of the microbial nucleic acid, and wherein the fluorescent signals from the second control nucleic acid are indicative of an amplification occurring in the amplifying step even in the absence of the fluorescent signals from the microbial nucleic acid.

The present invention further provides an analytical system additionally comprising a transfer module for transferring the biological sample from the sample preparation module to the reaction receptacle. In some embodiments, the first control nucleic acid is a quantitative standard nucleic acid and the second control nucleic acid is a qualitative internal control nucleic acid. In other embodiments, the methods comprise in step d) determining the quantity of the microbial nucleic acid in the biological sample by comparison of the signals generated by the microbial nucleic acid and the first control nucleic acid. A further embodiment employs a polymerase enzyme having 5' to 3' exonuclease activity. In another embodiment of the invention, the first control nucleic acid is present in a concentration of 20-5000 times the limit of detection of the microbial nucleic acid, and the second control nucleic acid is present in a concentration of 1-25 times the limit of detection of the microbial nucleic acid. In another embodiment of the invention, the first and second control nucleic acids are provided within one control reagent.

DESCRIPTION OF THE INVENTION

The present invention relates to new methods and uses for the simultaneous qualitative and quantitative detection of microbial nucleic acids. The method is based on amplification of nucleic acids, for example the polymerase chain reaction. In brief, specific sequence portions of the microbial nucleic acid and at least a first control nucleic acid are amplified and detected using one or more specific primer pairs. Thus, one subject of the invention is:

A method for simultaneously detecting and quantifying a microbial nucleic acid in a biological sample, said method comprising:
a) isolating and purifying said microbial nucleic acid
b) providing a reaction mixture comprising at least a first control nucleic acid, one or more primer pairs specifically hybridizing to distinct sequence portions of said microbial nucleic acid and to distinct sequence portions of said control nucleic acid, and probes specifically hybridizing to each of the sequences amplified by said one or more primer pairs, wherein said microbial nucleic acid and said control nucleic acid hybridize to different probes
c) adding said biological sample to said reaction mixture
d) performing one or more cycling steps, wherein a cycling step comprises an amplifying step, said amplifying step comprising producing one or more amplification products derived from said microbial nucleic acid if present in said sample and producing an amplification product derived from said control nucleic acid, and wherein a cycling step comprises a hybridizing step, said hybridizing step comprising hybridizing the sequences amplified by said primer pair with said probes, wherein the probes are labeled with a donor fluorescent moiety and a corresponding acceptor fluorescent moiety and each of the probes carries a different fluorescent dye
e) detecting and measuring fluorescent signals generated by said amplification products and being proportional to the concentration of said control nucleic acid and said microbial nucleic acid, wherein the presence of an amplification product of said control nucleic acid is indicative of an amplification occurring in the reaction mixture even in the absence of an amplification product for said microbial nucleic acid.

The present invention, for example, allows for a common design of qualitative and quantitative assays for any given microbial nucleic acid using identical reagents.

In some embodiments, the first control nucleic acid described above may serve as both an internal quantitative standard nucleic acid and a qualitative internal control nucleic acid. Thus, it abolishes the need for two separate tests or test kits, respectively. The performance of two separate tests puts a burden on the patient due to additional blood draws and potentially imposes additional costs on the healthcare systems in case the quantitative and the qualitative test are both reimbursed. Furthermore, the time-to-result for both a qualitative and a quantitative test is reduced when compared to sequential qualitative and quantitative experiments.

In some embodiments, said first control nucleic acid is evaluated according to different criteria for obtaining a qualitative and a quantitative result. In one embodiment, the same set of raw data obtained during real-time PCR is analyzed against two different test parameter settings. The qualitative test parameter settings applied for a valid qualitative control nucleic acid are more stringent as compared to the parameter settings applied for the internal quantitative standard needed for a quantitative result output. The settings for the internal quantitative standard nucleic acid in a quantitative reaction cannot be as stringent as the presence of target may affect the respective growth curves of the internal quantitative standard nucleic acid (see FIG. 1a).

Thus, another embodiment of the invention is the method described above, wherein the first control nucleic acid is analyzed according to different criteria in order to serve as a quantitative standard nucleic acid or as a qualitative internal control nucleic acid.

In other embodiments, it can be advantageous to employ a first and a second control nucleic acid in different concentrations due to the following reasons: Usually, the internal quantitative standard nucleic acid or acids in quantitative tests have a rather high concentration so that they are still amplified and detected in samples with a high concentration of target nucleic acid. Therefore, its usability as a control for the detection of low positive samples close to the limit of detection (LOD) is sometimes not given, especially if the amplification reaction is partly suppressed. In that case, the detection of a highly concentrated control nucleic acid cannot serve as a measure of sufficient sensitivity of the respective assay.

Thus, another aspect of the present invention is the following:

A method for simultaneously detecting and quantifying a microbial nucleic acid in a biological sample, said method comprising:
a) isolating and purifying said microbial nucleic acid
b) providing a reaction mixture comprising a first and a second control nucleic acid in different concentrations, one or more primer pairs specifically hybridizing to distinct sequence portions of said microbial nucleic acid and to distinct sequence portions of said control nucleic acids, and probes specifically hybridizing to each of the sequences amplified by said one or more primer pairs, wherein said microbial nucleic acid and said first control nucleic acid and said second control nucleic acid hybridize to different probes
c) adding said biological sample to said reaction mixture
d) performing one or more cycling steps, wherein a cycling step comprises an amplifying step, said amplifying step comprising producing one or more amplification products derived from said microbial nucleic acid if present in said sample and producing an amplification product derived from said first control nucleic acid and said second control nucleic acid, and wherein a cycling step comprises a hybridizing step, said hybridizing step comprising hybridizing the sequences amplified by said primer pair with said probes, wherein the probes are labeled with a donor fluorescent moiety and a corresponding acceptor fluorescent moiety and each of the probes carries a different fluorescent dye
e) detecting and measuring fluorescent signals generated by the amplification products of said first control nucleic acid and said microbial nucleic acid and being proportional to their concentration, and/or simultaneously detecting fluorescent signals generated by said amplification product of said second control nucleic acid, wherein the presence of an amplification product of said second control nucleic acid is indicative of an amplification occurring in the reaction mixture even in the absence of an amplification product for said microbial nucleic acid.

The exploitation of a first and a second control nucleic acid in different concentrations within the same control reagent, according to the present invention, overcomes the above-stated problem. The nucleic acid with the lower or lowest concentration corresponds to a qualitative internal control nucleic acid for a qualitative assay and ensures the ability to judge whether a negative result is valid or not, i.e. a negative result is not valid in case the internal control nucleic acid is not detected.

According to the present invention, the artisan can take advantage of the synergies between developing a quantitative and a qualitative setup by performing both in a single assay, thus reducing development costs, requiring less material and working force, reducing manufacturing costs and also cutting down the required time to establish an assay. Furthermore, double testing of patients putting burden on the patient due to additional blood draws is avoided as well as costs for the health care systems, where quantitative and qualitative test are both reimbursed, are reduced.

The qualitative internal control nucleic acid and/or the internal quantitative standard nucleic acid can be competitive, non-competitive or partially competitive.

"Competitive" means that, in an amplification reaction comprising primers, the respective control nucleic acid and the target nucleic acid or acids have at least essentially the same primer binding sites and thus compete for the same primers. Among the advantages of a competitive setup is, e.g., that fewer sets of different primers have to be introduced in the assay, thus reducing its costs and overall complexity. Furthermore, the functionality of the primers is monitored as are inhibition effects which are target primer specific.

"Non-competitive" means that the respective control nucleic acid and the target nucleic acid or acids have different primer binding sites and thus bind to different primers. Advantages of such a setup comprise, among others, the fact that the single amplification events of the different nucleic acids in the reaction mixture can take place independently from each other without any competition effects.

"Partially competitive" means that the respective control nucleic acid and at least one of the target nucleic acids compete for the same primers, while at least one other target nucleic acid binds to different primers.

By using an internal quantitative standard nucleic acid as a first control nucleic acid according to the method or methods of the invention, sample-specific, but also sample-unspecific inhibitory effects possibly interfering with the amplification and detection reactions for quantitative standard nucleic acid and microbial nucleic acid simultaneously (target region-independent inhibition) are leveled resulting in more accurate titers. "Internal" means that the first control nucleic acid is amplified, detected and quantified within the same reaction mixture as the microbial nucleic acid instead of in a separate experiment.

Another aspect of the invention is the method described supra, wherein the first control nucleic acid is a quantitative standard nucleic acid and the second control nucleic acid is a qualitative internal control nucleic acid.

The person skilled in the art can extract reliable qualitative, but optionally also equally reliable quantitative information from the same experiment. Therefore, in another aspect the invention relates to the following:

The method described above, further comprising in step e) determining the quantity of said microbial nucleic acid in said biological sample by comparison of the signals generated by said microbial nucleic acid and said first control nucleic acid.

In another embodiment, the first control nucleic acid and the second control nucleic acid have essentially the same sequence. In another embodiment, they have the same primer binding sites, but different probe binding sites.

This bears the advantage that the control nucleic acids for qualitative and quantitative measurements can based on the same selected binding sequence and share the same advantageous properties with respect to assay performance and in view of the analyte sequence or sequences.

Conventional techniques of molecular biology and nucleic acid chemistry, which are within the skill of the art, are explained in the literature. See, for example, Sambrook J. et al., Molecular Cloning: A Laboratory Manual, Cold Spring Harbor Laboratory Press, Cold Spring Harbor, N.Y., 1989, Gait, M. J., ed., 1984; Nucleic Acid Hybridization, Hames, B. D., and Higgins, S. J., eds., 1984; and a series, Methods in Enzymology, Academic Press, Inc.

"Simultaneously", in the sense of the invention, means that two actions, such as e.g. detecting and quantifying of a nucleic acid, are performed within the same reaction or reaction mixture.

A "reaction mixture" as used in the present invention comprises at least all components to facilitate a biological or chemical reaction. It is a single volume without any separating compartments, i.e. all components present in said "reaction mixture" are in immediate contact with each other.

A "biological sample" can be any sample of natural origin. An example of a "biological sample" is derived from a human and is a body liquid. In an embodiment of the invention, the "biological sample" is blood.

As is known in the art, a "nucleoside" is a base-sugar combination. The base portion of the nucleoside is normally a heterocyclic base. The two most common classes of such heterocyclic bases are the purines and the pyrimidines.

"Nucleotides" are "nucleosides" that further include a phosphate group covalently linked to the sugar portion of the nucleoside. For those "nucleosides" that include a pentofuranosyl sugar, the phosphate group can be linked to either the 2', 3' or 5' hydroxyl moiety of the sugar. A "nucleotide" is the "monomeric unit" of an "oligonucleotide", more generally denoted herein as an "oligomeric compound", or a "polynucleotide", more generally denoted as a "polymeric compound". Another general expression for the aforementioned is deoxyribonucleic acid (DNA) and ribonucleic acid (RNA).

According to the invention, an "oligomeric compound" is a compound consisting of "monomeric units" which may be "nucleotides" alone or "non-natural compounds" (see below), more specifically "modified nucleotides" (or "nucleotide analogs") or "non-nucleotide compounds", alone or combinations thereof. "Oligonucleotides" and "modified oligonucleotides" (or "oligonucleotide analogs") are subgroups of "oligomeric compounds" in the context of the invention.

In the context of this invention, the term "oligonucleotide" refers to "polynucleotides" formed from a plurality of "nucleotides" as the "monomeric unit", i.e. an "oligonucleotide" belongs to a specific subgroup of an "oligomeric compound" or "polymeric compound" of ribonucleic acid (RNA) or deoxyribonucleic acid (DNA) with "monomeric units". The phosphate groups are commonly referred to as forming the internucleoside backbone of the "oligonucleotide". The normal linkage or backbone of RNA and DNA is a 3' to 5' phosphodiester linkage.

"Oligonucleotides" and "modified oligonucleotides" (see below) according to the invention may be synthesized as principally described in the art and known to the expert in the field. Methods for preparing oligomeric compounds of specific sequences are known in the art, and include, for example, cloning and restriction of appropriate sequences and direct chemical synthesis. Chemical synthesis methods may include, for example, the phosphotriester method described by Narang S. A. et al., Methods in Enzymology 68 (1979) 90-98, the phosphodiester method disclosed by Brown E. L., et al., Methods in Enzymology 68 (1979) 109-151, the phosphoramidite method disclosed in Beaucage et al., Tetrahedron Letters 22 (1981) 1859, the H-phosphonate method disclosed in Garegg et al., Chem. Scr. 25 (1985) 280-282 and the solid support method disclosed in U.S. Pat. No. 4,458, 066.

For the above-described method, the nucleic acids can be present in double-stranded or single-stranded form whereby the double-stranded nucleic acids are denatured, i.e. made single-stranded, before the method is performed by heating, i.e. thermal denaturing.

In another embodiment, a primer and/or the probe may be chemically modified, i.e. the primer and/or the probe comprise a modified nucleotide or a non-nucleotide compound. The probe or the primer is then a modified oligonucleotide.

"Modified nucleotides" (or "nucleotide analogs") differ from a natural "nucleotide" by some modification but still consist of a base, a pentofuranosyl sugar, a phosphate portion, base-like, pentofuranosyl sugar-like and phosphate-like portion or combinations thereof. For example, a "label" may be attached to the base portion of a "nucleotide" whereby a "modified nucleotide" is obtained. A natural base in a "nucleotide" may also be replaced by e.g. a 7-deazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

A "non-nucleotide compound" is different from a natural "nucleotide" but is in the sense of this invention still capable—similar to a "nucleotide"—of being a "monomeric unit" of an "oligomeric compound". Therefore, a "non-nucleotide compound" has to be capable of forming an "oligomeric compound" with "nucleotides". Even "non-nucleotide compounds" may contain base-like, pentofuranosyl sugar-like or phosphate-like portions, however, not all of them are present at the same time in a "non-nucleotide compound".

A "modified oligonucleotide" (or "oligonucleotide analog"), belonging to another specific subgroup of the "oligomeric compounds", possesses one or more "nucleotides", one or more "non-nucleotide compounds" or "modified nucleotides" as "monomeric units". Thus, the term "modified oligonucleotide" (or "oligonucleotide analog") refers to structures that function in a manner substantially similar to "oligonucleotides" and is used interchangeably throughout the application. From a synthetic point of view, a "modified oligonucleotide" (or a "oligonucleotide analog") can for example be made by chemical modification of "oligonucleotides" by appropriate modification of the phosphate backbone, ribose unit or the nucleotide bases (Uhlmann and Peyman, Chemical Reviews 90 (1990) 543; Verma S., and Eckstein F., Annu. Rev. Biochem. 67 (1998) 99-134). Representative modifications include phosphorothioate, phosphorodithioate, methyl phosphonate, phosphotriester or phosphoramidate inter-nucleoside linkages in place of phosphodiester inter-nucleoside linkages; deaza- or aza-purines and -pyrimidines in place of natural purine and pyrimidine bases, pyrimidine bases having substituent groups at the 5 or 6 position; purine bases having altered substituent groups at the 2, 6 or 8 positions or 7 position as 7-deazapurines; bases carrying alkyl-, alkenyl-, alkinyl or aryl-moieties, e.g. lower alkyl groups such as methyl, ethyl, propyl, butyl, tert-butyl, pentyl, hexyl, heptyl, octyl, nonyl, decyl, or aryl groups like phenyl, benzyl, naphtyl; sugars having substituent groups at, for example, their 2' position; or carbocyclic or acyclic sugar analogs. Other modifications consistent with the spirit of this invention are known to those skilled in the art. Such "modified oligonucleotides" (or "oligonucleotide analogs") are best described as being functionally interchangeable with, yet structurally different from, natural "oligonucleotides" (or synthetic "oligonucleotides" along natural lines). In more detail, exemplary modifications are disclosed in Verma S., and Eckstein F., Annu. Rev. Biochem. 67 (1998) 99-134 or WO 02/12263. In addition, modification can be made wherein nucleoside units are joined through groups that substitute for the internucleoside phosphate or sugar phosphate linkages. Such linkages include those disclosed in Verma S., and Eckstein F., Annu. Rev. Biochem. 67 (1998) 99-134. When other than phosphate linkages are utilized to link the nucleoside units, such structures have also been described as "oligonucleosides".

A "nucleic acid" as well as the "target nucleic acid" or the "microbial nucleic acid" is a polymeric compound of "nucleotides" as known to the expert skilled in the art. "Target nucleic acid" or "microbial nucleic acid" is used herein to denote a "nucleic acid" in a sample which should be analyzed, i.e. the presence, non-presence and/or amount thereof in a sample should be determined. Therefore, in this case the nucleic acid is the target and can therefore be also denoted as "target nucleic acid". Since, according to the invention, the target nucleic acid is of microbial origin, the target nucleic acid is also referred to as "microbial nucleic acid". For example, if it has to be determined whether blood contains HCV, the "target nucleic acid" or "microbial nucleic acid" is the nucleic acid of HCV.

"Microorganism" means any virus, bacterium, archaean, fungus or any unicellular eukaryotic organism.

"Microbial" means derived from or belonging to a "microorganism".

"Detecting" means determining the presence or absence of a specific object, such as a target, or signal.

"Quantifying" means determining the quantity of a specific object, such as a target, or signal.

"Measuring" means determining at least a relative value of a specific object, such as a target, or signal.

In the sense of certain embodiments of the invention using a first and a second control nucleic acid, the first control nucleic acid serves as an "internal quantitative standard nucleic acid". An "internal quantitative standard nucleic acid" is a "nucleic acid" and thus a polymeric compound of "nucleotides" as known to the expert skilled in the art. In the case of the "internal quantitative standard nucleic acid", the nucleic acid is apt to be and used simultaneously as control for the validity of the reaction and as a reference in order to "quantify", i.e. to determine the quantity of the "target nucleic acid" or "microbial nucleic acid". For this purpose, the "internal quantitative standard nucleic acid" undergoes all possible sample preparation steps along with the "target nucleic acid" or the "microbial nucleic acid". Moreover, it is processed throughout the method within the same reaction mixture. The "internal quantitative standard nucleic acid" must generate, directly or indirectly, a detectable signal both in the presence or absence of the target nucleic acid. For this purpose, the concentration of the "internal quantitative standard nucleic acid" has to be carefully optimized in each test in order not to interfere with sensitivity but in order to generate a detectable signal also e.g. at very high target concentrations. For example, the concentration range for the "internal quantitative standard nucleic acid", i.e. the first control nucleic acid, will comprise a range of 100 copies per reaction to 100 000 copies per reaction. Possible concentrations of the "internal quantitative standard nucleic acid" may be e.g. for HIV: 1000 copies/reaction, for HCV: 7500 copies/reaction, but these concentrations may be adapted to the specific assay as known by the person skilled in the art. In terms of the limit of detection (LOD) of the respective assay, the concentration range for the "internal quantitative standard nucleic acid" is for example 20-5000×LOD, or 20-1000×LOD, or 20-500×LOD. The final concentration of the "internal quantitative standard nucleic acid" in the reaction mixture is dependent on the quantitative measuring range accomplished. The "internal quantitative standard nucleic acid" can be, for example, DNA, RNA or PNA, armored DNA or armored RNA and modified forms thereof.

Further, in the sense of the invention, the second control nucleic acid serves as a "qualitative internal control nucleic acid". A "qualitative internal control nucleic acid" is particularly important for confirming the validity of the test result of a qualitative detection assay: At least in the case of a negative result, the qualitative internal control nucleic acid must be detected, otherwise the test itself is considered to be inoperative. However, in a qualitative setup, the qualitative internal control nucleic acid does not necessarily have to be detected in case of a positive result. For qualitative tests, it is important that the sensitivity of the reaction is guaranteed and thus strictly controlled. As a consequence, the concentration of the qualitative internal control nucleic acid must be relatively low, such that even in a situation of slight inhibition the test is considered invalid. It has to be carefully adapted to the respective assay and its sensitivity. For example, the concentration range for the "qualitative internal nucleic acid", i.e. the second control nucleic acid, comprises a range of 1 copy per reaction to 1000 copies per reaction. In relation to the respective assay's limit of detection (LOD), its concentration is for example between the LOD of an assay and the 25fold value of the LOD. In another example, it is between 2× and 20×LOD, or between 2× and 15×LOD, or between 2× and 10×LOD. In another embodiment, it is between 3× and 7×LOD.

"Limit of detection" or "LOD" means the lowest detectable amount or concentration of a nucleic acid in a sample with a predefined hitrate. A low "LOD" corresponds to high sensitivity and vice versa. The "LOD" is usually expressed either by means of the unit "cp/ml", particularly if the nucleic acid is a viral nucleic acid, or as IU/ml. "Cp/ml" means "copies per milliliter" wherein a "copy" is copy of the respective nucleic acid. IU/ml stands for "International units/ml", referring to the WHO standard. Depending on the target, LOD values in clinical molecular diagnostic assays are typically below 1000 cp/ml. In example, the LOD in assays performed in the context of the invention is between 1 and 500 cp/ml.

A widely used method for calculating an LOD is "Probit Analysis", which is a method of analyzing the relationship between a stimulus (dose) and the quantal (all or nothing) response. In a typical quantal response experiment, groups of animals are given different doses of a drug. The percent dying at each dose level is recorded. These data may then be analyzed using Probit Analysis. The Probit Model assumes that the percent response is related to the log dose as the cumulative normal distribution. That is, the log doses may be used as variables to read the percent dying from the cumulative normal. Using the normal distribution, rather than other probability distributions, influences the predicted response rate at the high and low ends of possible doses, but has little influence near the middle.

The "Probit Analysis" can be applied at distinct "hitrates". As known in the art, "hitrate" is commonly expressed in percent [%] and indicates the percentage of positive results at a specific concentration of an analyte. Thus for example, an LOD can be determined at 95% hitrate, which means that the LOD is calculated for a setting in which 95% of the valid results are positive.

The term "primer" is used herein as known to the expert skilled in the art and refers to "oligomeric compounds", primarily to "oligonucleotides", but also to "modified oligonucleotides" that are able to "prime" DNA synthesis by a template-dependent DNA polymerase, i.e. the 3'-end of the e.g. oligonucleotide provides a free 3'-OH group whereto further "nucleotides" may be attached by a template-dependent DNA polymerase establishing 3' to 5' phosphodiester linkage whereby deoxynucleoside triphosphates are used and whereby pyrophosphate is released.

The term "probe", in the context of the invention, is also an oligonucleotide, but with a specific function: It hybridizes to other nucleic acids in a reaction mixture, in order to enable their detection. Thus, for example the probes specifically bind to certain nucleic acids. A probe carries, for example, at least one label. Probes can e.g. be labeled with different dyes, such that the respective probes can be detected and measured independently from each other.

"Labels", often referred to as "reporter groups", are generally groups that make a nucleic acid, in particular the "oligomeric compound" or the "modified oligonucleotide", as well as any nucleic acids bound thereto distinguishable from the remainder of the sample (nucleic acids having attached a "label" can also be termed labeled nucleic acid binding compounds, labeled probes or just probes). Labels according to the invention can include for example fluorescent labels, which are e.g. "fluorescent dyes" as a fluorescein dye, a rhodamine dye, a cyanine dye, and a coumarin dye. Exemplary "fluorescent dyes" according to the invention are FAM, HEX, CY5, JA270, Cyan, CY5.5, LC-Red 640, LC-Red 705.

For the above-described method, the nucleic acids can be present in double-stranded or single-stranded form whereby the double-stranded nucleic acids are denatured, i.e. made single-stranded, before the method is performed by heating, i.e. thermal denaturing.

In another embodiment, a primer and/or the probe may be chemically modified, i.e. the primer and/or the probe comprise a modified nucleotide or a non-nucleotide compound. The probe or the primer is then a modified oligonucleotide.

A "detectable signal" is a signal "generated", by a compound such as the "microbial nucleic acid", the "internal control nucleic acid" or the "quantitative standard nucleic acid", rendering said compound distinguishable from the remainder of the sample. According to the invention, said "detectable signal" can be quantified or analyzed in a qualitative manner. A "detectable signal" can be e.g. radioactive or optical such as luminescent signals. For example, "detectable signals" according to the invention can be fluorescent signals emitted by "fluorescent dyes".

"Inhibition" or "suppression" of a PCR reaction denotes a PCR reaction which is less efficient as compared to the standard reaction observed in the majority of samples. The "inhibition" or "suppression" effect can be seen in either reduced fluorescence levels of growth curves for control and/or target, in delayed CT values, in changes of the slope of the growth curve, in changes in the turning point or other features of the reaction characteristics. The "inhibition" or "suppression" effect can result from varied sample preparation efficacy, sample-related effects, the possible and often not predictable presence of agents inhibiting the amplification and/or detection reaction, and other reasons. Therefore, it might be the case that a sample is judged as negative due to an unsuccessful extraction procedure or other sample-based factors, whereas the microbial nucleic acid to be detected and quantified is actually present in the sample.

"To generate" means to produce, directly or indirectly. In the context of a "detectable signal", "to generate" can therefore mean "to produce directly", e.g. in the case of a fluorescent dye emitting a fluorescent signal, or "to produce indirectly" in the sense of "to evoke" or "to induce", such as a "microbial nucleic acid" "generating" a "detectable signal" via a "label" such as a "fluorescent dye", or via a nucleic acid probe carrying a "label" such as a "fluorescent dye".

As known by the person skilled in the art, the terms "specific" or "specifically hybridizing" in the context of primers and probes implies that a primer or probe "specific" for a distinct nucleic acid binds to said nucleic acid under stringent conditions. For example, the primers and probes used in the method according to the invention are at least 80% identical to sequence portions of the microbial nucleic acid and/or the first and second control nucleic acid.

The "Polymerase Chain Reaction" (PCR) is disclosed, among other references, in U.S. Pat. Nos. 4,683,202, 4,683,195, 4,800,159, and 4,965,188 and is an exemplary nucleic acid amplification technique used for method according to the invention. PCR typically employs two or more oligonucleotide primers that bind to a selected nucleic acid template (e.g. DNA or RNA). Primers useful in the present invention include oligonucleotides capable of acting as a point of initiation of nucleic acid synthesis within the nucleic acid sequences of the microbial nucleic acid or quantitative standard nucleic acid. A primer can be purified from a restriction digest by conventional methods, or it can be produced synthetically. The primer is for example single-stranded for maximum efficiency in amplification, but the primer can be double-stranded. Double-stranded primers are first denatured, i.e., treated to separate the strands. One method of denaturing double stranded nucleic acids is by heating. A "thermostable polymerase" is a polymerase enzyme that is heat stable, i.e., it is an enzyme that catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished. If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 3 sec to 4 min (e.g., 5 sec to 2 min 30 sec, or 10 sec to 1.5 min). If the double-stranded template nucleic acid is denatured by heat, the reaction mixture is allowed to cool to a temperature that promotes annealing of each primer to its target sequence on the microbial nucleic acid and/or internal standard nucleic acid. The temperature for annealing is usually from about 35° C. to about 75° C. (e.g., about 40° C. to about 70° C.; about 45° C. to about 66° C.). Annealing times can be from about 5 sec to about 1 min (e.g., about 10 sec to about 50 sec; about 15 sec to about 40 sec The reaction mixture is then adjusted to a temperature at which the activity of the polymerase is promoted or optimized, i.e., a temperature sufficient for extension to occur from the annealed primer to generate products complementary to the microbial nucleic acid and/or internal standard nucleic acid. The temperature should be sufficient to synthesize an extension product from each primer that is annealed to a nucleic acid template, but should not be so high as to denature an extension product from its complementary template (e.g., the temperature for extension generally ranges from about 35° to 80° C. (e.g., about 40° C. to about 75° C.; about 45° C. to 72° C.). Extension times can be from about 5 sec to about 5 min (e.g., about 10 sec to about 3 min; about 15 sec to about 2 min; about 20 sec to about 1 min). The newly synthesized strands form a double-stranded molecule that can be used in the succeeding steps of the reaction. The steps of strand separation, annealing, and elongation can be repeated as often as needed to produce the desired quantity of amplification products corresponding to the microbial nucleic acid and/or quantitative standard nucleic acid. The limiting factors in the reaction are the amounts of primers, thermostable enzyme, and nucleoside triphosphates present in the reaction. The cycling steps (i.e., denaturation, annealing, and extension) are repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Nucleic acid amplification reactions apart from PCR comprise the Ligase Chain Reaction (LCR; Wu D. Y. and Wallace R. B., Genomics 4 (1989) 560-69; and Barany F., Proc. Natl. Acad. Sci. USA 88 (1991) 189-193); Polymerase Ligase Chain Reaction (Barany F., PCR Methods and Applic. 1 (1991) 5-16); Gap-LCR (WO 90/01069); Repair Chain Reaction (EP 0439182 A2), 3SR (Kwoh D. Y. et al., Proc. Natl. Acad. Sci. USA 86 (1989) 1173-1177; Guatelli J. C., et al., Proc. Natl. Acad. Sci. USA 87 (1990) 1874-1878; WO 92/08808), and NASBA (U.S. Pat. No. 5,130,238). Further, there are strand displacement amplification (SDA), transcription mediated amplification (TMA), and Q-beta-amplification (for a review see e.g. Whelen A. C. and Persing D. H., Annu Rev. Microbiol. 50 (1996) 349-373; Abramson R. D. and Myers T. W., Curr Opin Biotechnol 4 (1993) 41-47).

Suitable nucleic acid detection methods are known to the expert in the field and are described in standard textbooks as Sambrook J. et al., Molecular Cloning: A Laboratory Manual, Cold Spring Harbor Laboratory Press, Cold Spring Harbor, N.Y., 1989 and Ausubel F. et al.: Current Protocols in Molecular Biology 1987, J. Wiley and Sons, NY. There may be also further purification steps before the nucleic acid detection step is carried out as e.g. a precipitation step. The detection methods may include but are not limited to the binding or intercalating of specific dyes as ethidium bromide which intercalates into the double-stranded DNA and changes its fluorescence thereafter. The purified nucleic acid may also be separated by electrophoretic methods optionally after a restriction digest and visualized thereafter. There are also probe-based assays which exploit the oligonucleotide hybridization to specific sequences and subsequent detection of the hybrid. It is also possible to sequence the nucleic acid after further steps known to the expert in the field. An example of a template-dependent nucleic acid polymerase is the Z05 DNA polymerase and mutations thereof. Other template-dependent nucleic acid polymerases useful in the invention are Taq polymerase and Tth Polymerase. Yet other nucleic acid polymerases useful for the methods according to the invention are known to the skilled artisan.

In the context of the invention, the microbial nucleic acid and each of the control nucleic acids bind to different probes carrying different labels in order to render them distinguishable from one another during detection. Hence, said different probes can carry different fluorescent dyes, emitting fluorescent light at different wavelengths. These different fluorescence signals can be advantageously detected independently from each other in different channels of a fluorescence detector as used in most devices for performing real time PCR.

Also for example, results for the microbial nucleic acid, the first control nucleic acid and the second control nucleic acid are visualized on a display in different masks, or in different displays.

In the sense of the invention, "purification", "isolation" or extraction" of nucleic acids relate to the following: Before nucleic acids may be analyzed in one of the above-mentioned assays, they have to be purified, isolated or extracted from biological samples containing complex mixtures of different components. Often, for the first steps, processes are used which allow the enrichment of the nucleic acids. To release the contents of cells or viral particles, they may be treated with enzymes or with chemicals to dissolve, degrade or denature the cellular walls or viral particles. This process is commonly referred to as lysis. The resulting solution containing such lysed material is referred to as lysate. A problem often encountered during lysis is that other enzymes degrading the component of interest, e.g. deoxyribonucleases or ribonucleases degrading nucleic acids, come into contact with the component of interest during the lysis procedure. These degrading enzymes may also be present outside the cells or may have been spatially separated in different cellular compartments prior to lysis. As the lysis takes place, the component of interest becomes exposed to said degrading enzymes. Other components released during this process may e.g. be endotoxins belonging to the family of lipopolysaccharides which are toxic to cells and can cause problems for products intended to be used in human or animal therapy.

There is a variety of means to tackle the above-mentioned problem. It is common to use chaotropic agents such as guanidinium thiocyanate or anionic, cationic, zwitterionic or non-ionic detergents when nucleic acids are intended to be set free. It is also an advantage to use proteases which rapidly degrade the previously described enzymes or unwanted proteins. However, this may produce another problem as said substances or enzymes can interfere with reagents or components in subsequent steps.

Enzymes which can be advantageously used in such lysis or sample preparation processes mentioned above are enzymes which cleave the amide linkages in protein substrates and which are classified as proteases, or (interchangeably) peptidases (see Walsh, 1979, Enzymatic Reaction Mechanisms. W. H. Freeman and Company, San Francisco, Chapter 3). Proteases used in the prior art comprise alkaline proteases (WO 98/04730) or acid proteases (U.S. Pat. No. 5,386,024). A protease which has been widely used for sample preparation in the isolation of nucleic acids in the prior art is proteinase K from Tritirachium album (see e.g. Sambrook J. et al., Molecular Cloning: A Laboratory Manual, Cold Spring Harbor Laboratory Press, Cold Spring Harbor, N.Y., 1989) which is active around neutral pH and belongs to a family of proteases known to the person skilled in the art as subtilisins. Especially advantageous for the use in lysis or sample preparation processes mentioned above is the enzyme esperase, a robust protease that retains its activity at both high alkalinity and at high temperatures (EP 1 201 753).

In the sample preparation steps following the lysis step, the component of interest is further enriched.

If the non-proteinaceous components of interest are e.g. nucleic acids, they are normally extracted from the complex lysis mixtures before they are used in a probe-based assay.

There are several methods for the purification of nucleic acids, for example:
sequence-dependent or biospecific methods as e.g.:
affinity chromatography
hybridization to immobilized capture oligonucleotides
sequence-independent or physico-chemical methods as e.g.:
liquid-liquid extraction with e.g. phenol-chloroform
precipitation with e.g. pure ethanol
extraction with filter paper
extraction with micelle-forming agents as cetyl-trimethyl-ammonium-bromide
binding to immobilized, intercalating dyes, e.g. acridine derivatives
adsorption to silica gel or diatomic earths
adsorption to magnetic glass particles (MGP) or organosilane particles under chaotropic conditions Particularly interesting for purification purposes is the adsorption of nucleic acids to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface is preferred because, among other reasons, the nucleic acids do not have to be modified, and even native nucleic acids can be bound. These processes are described in detail by various documents. In Vogelstein B. et al., Proc. Natl. Acad. USA 76 (1979) 615-9, for instance, a procedure for binding nucleic acids from agarose gels in the presence of sodium iodide to ground flint glass is proposed. The purification of plasmid DNA from bacteria on glass dust in the presence of sodium perchlorate is described in Marko M. A. et al., Anal. Biochem. 121 (1982) 382-387. In DE-A 37 34 442, the isolation of single-stranded M13 phage DNA on glass fiber filters by precipitating phage particles using acetic acid and lysis of the phage particles with perchlorate is described. The nucleic acids bound to the glass fiber filters are washed and then eluted with a methanol-containing Tris/EDTA buffer. A similar procedure for purifying DNA from lambda phages is described in Jakobi R. et al., Anal. Biochem. 175 (1988) 196-201. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. This is a limiting step, however, that prevents the procedure from being used to process large quantities of samples. The use of magnetic particles to immobilize nucleic acids after precipitation by adding salt and ethanol is more advantageous and described e.g. in Alderton R. P. et al., S., Anal. Biochem. 201 (1992) 166-169 and PCT GB 91/00212. In this procedure, the nucleic acids are agglutinated along with the magnetic particles. The agglutinate is separated from the original solvent by applying a magnetic field and performing a wash step. After one wash step, the nucleic acids are dissolved in a Tris buffer. This procedure has a disadvantage, however, in that the precipitation is not selective for nucleic acids. Rather, a variety of solid and dissolved substances are agglutinated as well. As a result, this procedure cannot be used to remove significant quantities of any inhibitors of specific enzymatic reactions that may be present. Magnetic, porous glass is also available on the market that contains magnetic particles in a porous, particular glass matrix and is covered with a layer containing streptavidin. This product can be used to isolate biological materials, e.g., proteins or nucleic acids, if they are modified in a complex preparation step so that they bind covalently to biotin. Magnetizable particular adsorbents proved to be very efficient and suitable for automatic sample preparation. Ferrimagnetic and ferromagnetic as well as superparamagnetic, pigments are used for this purpose. MGPs and methods using magnetic glass particles are, for example, those described in WO 01/37291. Particularly useful for the nucleic acid isolation in the context of the invention is the method according to R. Boom et al. (J Clin Microbiol. 28 (1990), 495-503).

After the purification or isolation of the nucleic acids including the target nucleic acid from their natural surroundings, the target nucleic acid may be detected.

In an embodiment, the method of the invention includes steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next. In addition, standard laboratory containment practices and procedures are desirable when performing the method of the invention. Containment practices and procedures include, but are not limited to, separate work areas for different steps of a method, containment hoods, barrier filter pipette tips and dedicated air displacement pipettes. Consistent containment practices and procedures by personnel are necessary for accuracy in a diagnostic laboratory handling clinical samples.

The methods set out above can be based on Fluorescence Resonance Energy Transfer (FRET) between a donor fluorescent moiety and an acceptor fluorescent moiety. A representative donor fluorescent moiety is fluorescein, and representative corresponding acceptor fluorescent moieties include LC-Red 640, LC-Red 705, Cy5, and Cy5.5. Typically, the detecting step includes exciting the sample at a wavelength absorbed by the donor fluorescent moiety and visualizing and/or measuring the wavelength emitted by the corresponding acceptor fluorescent moiety. According to the invention, the detection is followed by quantitating the FRET. For example, the detecting step is performed after each cycling step. For example, the detecting step is performed in real time. By using commercially available real-time PCR instrumentation (e.g., LightCycler™ or TaqMan®), PCR amplification and detection of the amplification product can be combined in a single closed reaction compartment such as, e.g., a cuvette with dramatically reduced cycling time. Since detection occurs concurrently with amplification, the real-time PCR methods obviate the need for manipulation of the amplification product, and diminish the risk of cross-contamination between amplification products. Real-time PCR greatly reduces turn-around time and is an attractive alternative to conventional PCR techniques in the clinical laboratory.

In example, the following patent applications describe real-time PCR as used in the LightCycler™ technology: WO 97/46707, WO 97/46714 and WO 97/46712. The LightCycler™ instrument is a rapid thermal cycler combined with a microvolume fluorometer utilizing high quality optics. This rapid thermocycling technique uses thin glass cuvettes as reaction vessels. Heating and cooling of the reaction chamber are controlled by alternating heated and ambient air. Due to the low mass of air and the high ratio of surface area to volume of the cuvettes, very rapid temperature exchange rates can be achieved within the thermal chamber.

TaqMan® technology utilizes a single-stranded hybridization probe labeled with two fluorescent moieties. When a first fluorescent moiety is excited with light of a suitable wavelength, the absorbed energy is transferred to a second fluorescent moiety according to the principles of FRET. The second fluorescent moiety is generally a quencher molecule. Typical fluorescent dyes used in this format are for example, among others, FAM, HEX, CY5, JA270, Cyan and CY5.5. During the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as the Z05 polymerase, during the subsequent elongation phase. As a result, the excited fluorescent moiety and the quencher moiety become spatially separated from one another. As a consequence, upon excitation of the first fluorescent moiety in the absence of the quencher, the fluorescence emission from the first fluorescent moiety can be detected.

In both detection formats described above, the intensity of the emitted signal can be correlated with the number of original target nucleic acid molecules.

As an alternative to FRET, an amplification product can be detected using a double-stranded DNA binding dye such as a fluorescent DNA binding dye (e.g., SYBRGREEN I® or SYBRGOLD® (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

Molecular beacons in conjunction with FRET can also be used to detect the presence of an amplification product using the real-time PCR methods of the invention. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the amplification products, the secondary structure of the probe is disrupted and the fluorescent moieties become separated from one another such that after excitation with light of a suitable wavelength, the emission of the first fluorescent moiety can be detected.

Thus, in a method according to the invention is the method described above using FRET, wherein said probes comprise a nucleic acid sequence that permits spatial proximity between said first and second fluorescent moiety.

Efficient FRET can only take place when the fluorescent moieties are in direct local proximity and when the emission spectrum of the donor fluorescent moiety overlaps with the absorption spectrum of the acceptor fluorescent moiety.

Thus, in an embodiment of the invention, said donor and acceptor fluorescent moieties are within no more than 5 nucleotides of each other on said probe.

In a further embodiment, said acceptor fluorescent moiety is a quencher.

As described above, in the TaqMan format, during the annealing step of the PCR reaction, the labeled hybridization probe binds to the target nucleic acid (i.e., the amplification product) and is degraded by the 5' to 3' exonuclease activity of the Taq or another suitable polymerase as known by the skilled artisan, such as the Z05 polymerase, during the subsequent elongation phase.

Thus, in an embodiment, in the method according to the invention, amplification employs a polymerase enzyme having 5' to 3' exonuclease activity.

The method according to the invention can be advantageously applied on viral nucleic acids. Thus, in an embodiment of the invention, the microbial nucleic acid is a viral nucleic acid.

Among viral nucleic acids, the method according to the invention can be advantageously be applied on HCV. Thus, in an embodiment of the invention, the microbial nucleic acid is a nucleic acid of HCV. However, it must be understood that the invention can also be applied on any other microbial nucleic acid.

An example how to perform calculation of quantitative results in the TaqMan format based on an internal standard is described in the following. A titer is calculated from input data of instrument-corrected fluorescence values from an entire PCR run. A set of samples containing a target nucleic acid such as a microbial nucleic acid and a first control nucleic acid serving as an internal quantitative standard nucleic acid undergo PCR on a thermocycler using a temperature profile as specified. At selected temperatures and times during the PCR profile samples are illuminated by filtered light and the filtered fluorescence data are collected for each sample for the target nucleic acid and the internal quantitative standard nucleic acid. After a PCR run is complete, the fluorescence readings are processed to yield one set of dye concentration data for the internal quantitative standard nucleic acid and one set of dye concentration data for the target nucleic acid. Each set of dye concentration data is processed in the same manner.

After several plausibility checks, the elbow values (CT) are calculated for the internal quantitative standard nucleic acid and the target nucleic acid. The elbow value is defined as the point where the fluorescence of the target nucleic acid or the internal quantitative standard nucleic acid crosses a predefined threshold (fluorescence concentration). Titer determination is based on the assumptions that the target nucleic acid and the internal quantitative standard nucleic acid are amplified with the same efficiency and that at the calculated elbow value equal amounts of amplicon copies of target nucleic acid and quantitative standard nucleic acid are amplified and detected. Therefore, the (CTQS−CTtarget) is linear to log (target conc/QS conc), wherein "QS" stands for the internal quantitative standard nucleic acid. The titer T can then be calculated for instance by using a polynomial calibration formula as in the following equation:

$$T' = 10(a(CTQS-CTtarget)2 + b(CTQS-CTtarget) + c)$$

The polynomial constants and the concentration of the internal quantitative standard nucleic acid are known, therefore the only variable in the equation is the difference (CTQS−CTtarget).

An example how to perform calculation of qualitative results in the TaqMan is described in the following: Input data of instrument-corrected fluorescence values from an entire PCR run are analyzed. A set of samples possibly containing a target nucleic acid such as a microbial nucleic acid and a control nucleic acid serving as a qualitative internal control nucleic acid undergo PCR on a thermocycler using a temperature profile as specified. At selected temperatures and times during the PCR profile samples are illuminated by filtered light and the filtered fluorescence data are collected for each sample for the target nucleic acid and the qualitative internal control nucleic acid. After a PCR run is complete, the fluorescence readings are processed to yield one set of dye concentration data for the qualitative internal control nucleic acid and one set of dye concentration data for the target nucleic acid. Each set of dye concentration data is processed in the same manner. The elbow values (CT) are calculated for the qualitative internal control nucleic acid and, if present, the target nucleic acid. The elbow value is defined as the point where the fluorescence of the target nucleic acid or the internal quantitative standard nucleic acid crosses a predefined threshold (fluorescence concentration). The qualitative internal control is valid if a CT within specified ranges is obtained and if the fluorescence rises above a predefined minimum fluorescence intensity. If no target CT is obtained, the qualitative internal control must be valid. If a target CT is obtained indicating presence of target nucleic acid in the sample, the qualitative internal control can be valid or invalid.

Embodiments of the invention are any of the methods described above, wherein said first and said second control nucleic acid are provided within one control reagent.

The concept of a control reagent with a first and a second control nucleic acid in different concentrations for reliable qualitative detection and at the same time for reliable quantification can be advantageously used for any respective assay targeting a microbial nucleic acid.

Thus, another aspect of the invention is the use of a first and a second control nucleic acid in different concentrations for simultaneously detecting and quantifying a microbial nucleic acid by real time PCR. Further for example is the use described above, wherein said first and second control nucleic acid are amplified by the same primer pair or different primer pairs but hybridize to different probes.

Particularly favorable is a use of this concept in the method according to the invention. Thus, in another aspect, the invention concerns the use of a first and a second control nucleic acid in different concentrations for simultaneously detecting and quantifying a microbial nucleic acid according to the method or methods described above.

The invention also provides a kit for simultaneously detecting and quantifying a microbial nucleic acid in a biological sample by real time PCR, said kit comprising a first and a second control nucleic acid in different concentrations, one or more primer pairs specifically hybridizing to distinct sequence portions of said microbial nucleic acid and to distinct sequence portions of said first and second control nucleic acid, and probes specifically hybridizing to each of the sequences amplified by said one or more primer pairs, wherein said first and second control nucleic acids are provided within one control reagent.

In an embodiment, the invention provides a kit for simultaneously detecting and quantifying a microbial nucleic acid in a biological sample according to any of the methods described supra, said kit comprising a first and a second control nucleic acid in different concentrations, one or more primer pairs specifically hybridizing to distinct sequence portions of said microbial nucleic acid and to distinct sequence portions of said first and second control nucleic acid, and probes specifically hybridizing to each of the sequences amplified by said one or more primer pairs.

A further aspect of the invention is a kit as described above, wherein said first and second control nucleic acid are amplified by the same primer pair but hybridize to different probes, thus providing for a competitive setup. However, it has to be understood that non- or partially competitive assays and kits for carrying out the respective methods are also comprised by the invention.

Such kits may further comprise, as known in the art, plastics ware which can be used during the sample preparation procedure as e.g. microtiter plates in the 96 or 384 well format or ordinary reaction tubes manufactured e.g. by Eppendorf, Hamburg, Germany and all other reagents for carrying out the method according to the invention. Therefore, the kit can additionally contain a material with an affinity to nucleic acids, for example the material with an affinity to nucleic acids comprises a material with a silica surface. Further for example, the material with a silica surface is a glass. Further for example, the material with an affinity to nucleic acids is a composition comprising magnetic glass particles. The kit can further or additionally comprise a protease reagent and a lysis buffer containing e.g. chaotropic agents, detergents or alcohols or mixtures thereof allowing for the lysis of cells. These components of the kit according to the invention may be provided separately in tubes or storage containers. Depending on the nature of the components, these may be even provided in a single tube or storage container. The kit may further or additionally comprise a washing solution which is suitable for the washing step of the magnetic glass particles when a nucleic acid is bound thereto. This washing solution may contain ethanol and/or chaotropic agents in a buffered solution or solutions with an acidic pH without ethanol and/or chaotropic agents as described above. Often the washing solution or other solutions are provided as stock solutions which have to be diluted before use. The kit may further or additionally comprise an eluent or elution buffer, i.e. a solution or a buffer (e.g. 10 mM Tris, 1 mM EDTA, pH 8.0) or pure water to elute the nucleic acid bound to the magnetic glass particles. Further, additional reagents or buffered solutions may be present which can be used for the purification process of a nucleic acid.

In another embodiment, the kit contains a polymerase enzyme having 5' to 3' exonuclease activity. Another embodiment is that the kit contains an enzyme with reverse transcriptase activity.

In another embodiment, the kit contains a polymerase enzyme having 5' to 3' exonuclease activity and reverse transcriptase activity.

In an embodiment of the invention, the method according to the invention is embedded in a sequence of methods carried out within an analytical system, thereby forming an automatable process.

Therefore, an aspect of the invention is the following:

An analytical system for simultaneously detecting and quantifying a microbial nucleic acid in a biological sample by real time PCR, said system comprising
- a sample preparation module comprising a lysis buffer and a vessel for isolating and purifying said microbial nucleic acid
- an amplification and detection module comprising a reaction receptacle in which the method described above is performed
- a kit as described above.

The sample preparation module can advantageously comprise components for the sample preparation procedures described supra, i.e. for example magnetic glass particles and a magnet for separating them from the solution, a protease reagent, chaotropic salt solutions and one or more vessels that contain the crude sample and the reagents required for sample preparation.

The reaction receptacle in the amplification and detection module can for example be a microtiter plate, a centrifugation vial, a lysis tube, or any other type of vessel suitable for containing a reaction mixture according to the invention.

In an embodiment of the invention, the analytical system contains a storage module containing the reagents for performing the method of the invention.

Said storage module can further contain other components useful for the method of the invention, e.g. disposables such as pipet tips or even vessels to be used as reaction receptacles within the amplification and detection module.

In an embodiment of the invention, the analytical system includes a preanalytical system module for transferring the biological sample from primary tubes to vessels usable on the analytical system.

In yet another embodiment of the invention, the analytical system contains a transfer module for transferring the biological sample from the sample preparation module to the amplification and detection module.

Even though it is possible to carry out said transfer manually, it is preferable to use an automated system wherein the transfer is performed e.g. by a robotic device such e.g. as a motor-driven mobile rack or robotic pivot arm.

Automatable process means that the steps of the process are suitable to be carried out with an apparatus or machine capable of operating with little or no external control or influence by a human being. Automated method means that the steps of the automatable method are carried out with an apparatus or machine capable of operating with little or no external control or influence by a human being. Only the preparation steps for the method may have to be done by hand, e.g. storage containers have to be filled and put into place, the choice of samples has to be performed by a human being and further steps known to the expert in the field, e.g. the operation of a controlling computer. The apparatus or machine may e.g. automatically add liquids, mix the samples or carry out incubation steps at specific temperatures. Typically, such a machine or apparatus is a robot controlled by a computer which carries out a program in which the single steps and commands are specified.

Thus, for example, the analytical system according to the invention further comprises a control unit for controlling system components.

Such a control unit may comprise a software for ensuring that the different components of said analytical system work and interact correctly and with the correct timing, e.g. moving components such as the sample to the reaction module in a coordinated manner. The control unit may also comprise a processor running a real-time operating system (RTOS), which is a multitasking operating system intended for real-time applications. In other words the system processor is capable of managing real-time constraints, i.e. operational deadlines from event to system response regardless of system load. It controls in real time that different units within the system operate and respond correctly according to given instructions.

All other embodiments and specific descriptions of embodiments of the uses, kits and analytical systems according to the invention are those mentioned for the method according to the invention.

DESCRIPTION OF THE FIGURES

FIG. 1a:

Figure 1A:
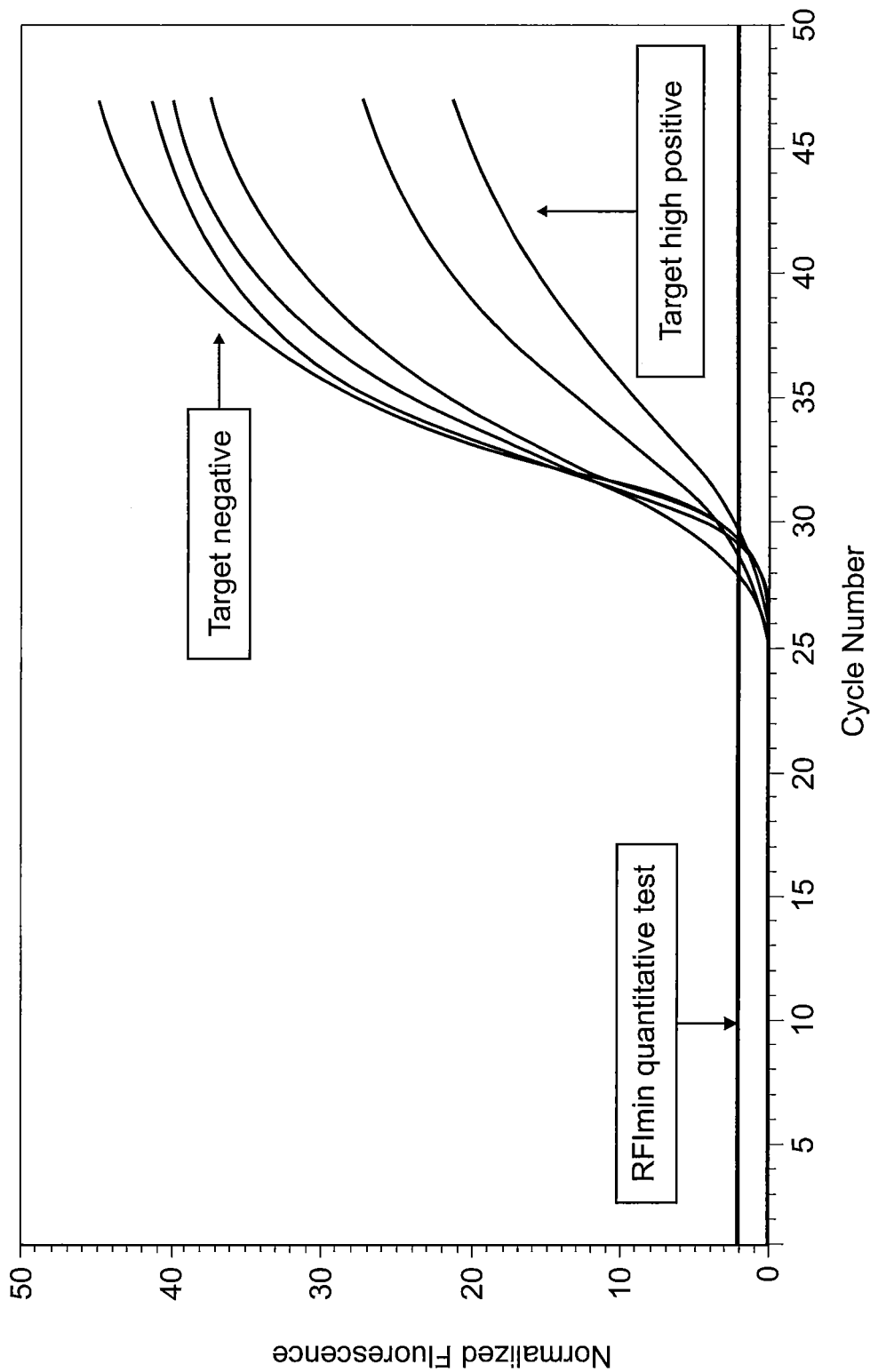
Figure 1B:
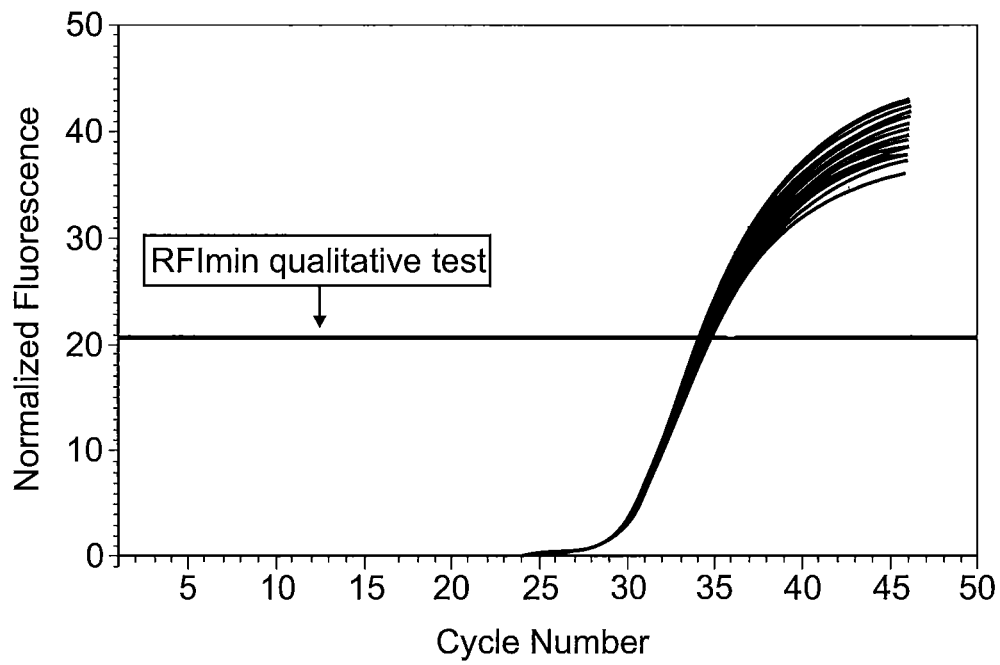

Internal control growth curves for quantitative real time PCR reactions of the commercial COBAS AmpliPrep/COBAS TaqMan HIV-1 test are shown in the graph. The PCR reactions contained HIV-1 target concentrations spanning a 5 log 10 range and a target negative sample. If high target concentrations are present in the reaction (see "Target high positive") the fluorescence level which is reached by the internal quantitative standard nucleic acid (QS) is significantly lower than in the case of PCR reactions with no HIV-1 target present (see "Target negative"). As the QS must be valid at all target concentrations in order to be able to calculate a titer for a quantitative result output, the minimal fluorescence intensity level setting ("RFImin") for the QS is low. RFImin settings for a quantitative result output in the three commercial tests COBAS AmpliPrep/COBAS TaqMan HBV, HCV and HIV-1 are given in Table 1.

FIG. 1b:

Internal control growth curves for real time PCR reactions of the commercial COBAS AmpliPrep/COBAS TaqMan HIV-1 test are shown in the graph. All PCR reactions contained HIV-1 target negative samples. The fluorescence level of the internal control growth curves is bundled within a narrow range and the minimal fluorescence intensity level setting ("RFImin") for the qualitative internal control nucleic acid (IC) is high. In target positive reactions the IC may fall below the RFImin and may become invalid; in the presence of target the result for the PCR reaction is still valid. RFImin settings as optimized for a qualitative result output for the tests COBAS AmpliPrep/COBAS TaqMan HBV, HCV and HIV-1 are given in Table 1.

FIG. 2:

Production of armored RNA particles: expression vector for the production of armored RNA particles and electron microscopy of armored RNA particles. Armored RNA particles are composed in *E. coli*. After induction of lac-Operon mRNA is transcribed that includes the MS-2 bacteriophage gene of MS-2 coat protein, the control sequence, a packaging signal and a the plasmid sequence upstream the TrrnB terminator. After the coat protein is translated, composition of the particle occurs spontaneously packing one copy of mRNA.

FIG. 3:

Normalized growth curves obtained for a real time PCR reaction containing HCV target, a first control nucleic acid and a second control nucleic acid.

FIG. 4a:

Simultaneous amplification of HCV-RNA and QS. The fluorescence intensity of both QS and HCV-RNA are lower than in a reaction leading to standard signals (see FIG. 4b).

FIG. 4b:

Simultaneous amplification of HCV-RNA and QS. Both reactions result in standard fluorescence intensities. For comparison see FIG. 4a with suppressed fluorescence curves, also note the different magnitude in the two figures.

EXAMPLES

The following examples are offered to illustrate, but not to limit the claimed invention.

Example 1

A First Control Nucleic Acid is Evaluated According to Different Criteria for Obtaining a Qualitative and a Quantitative Result Output The COBAS AmpliPrep/COBAS TaqMan HBV, HCV and HIV-1 tests are commercially available real-time PCR tests which have been optimized for accurate quantification of the viral targets HBV, HCV and HIV-1. The assays are used on either the fully automated COBAS AmpliPrep/COBAS TaqMan system including a docking station for the automated transfer of the PCR reaction mix from the sample preparation unit to the amplification/detection unit or on the COBAS AmpliPrep/COBAS TaqMan system with manual transfer or on the COBAS AmpliPrep/COBAS TaqMan 48 system.

Figure 4A:
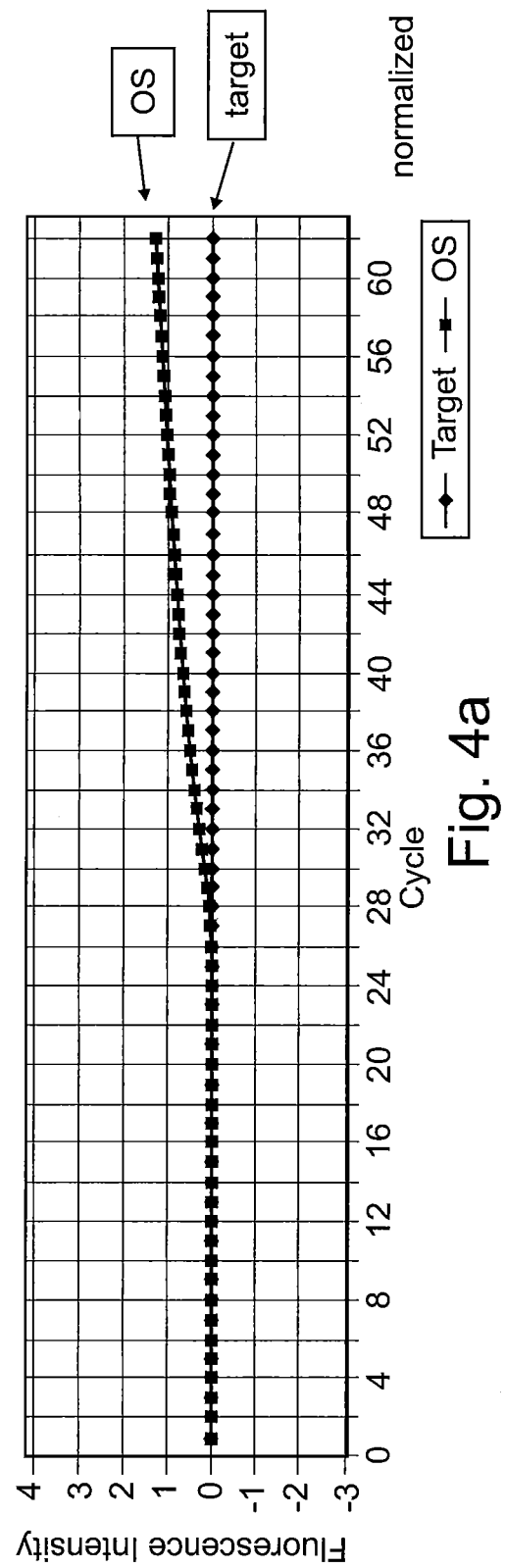

The COBAS AmpliPrep/COBAS TaqMan HCV test was used as an example to investigate the approach to provide simultaneous quantitative and qualitative test results with one set of identical reagents. The test has a Limit of Detection of 15 IU/mL and shows state of the art sensitivity, comparable or better to quantitative but also qualitative HCV tests on the market. Due to this high sensitivity there have been attempts to also use the test as qualitative HCV test. The main focus of a quantitative test is to provide accurate HCV titers whereas the main focus of a qualitative test is to ensure high sensitivity of the assay. As the COBAS AmpliPrep/COBAS TaqMan HCV test originally was developed for quantitative monitoring of treatment success an analysis was conducted whether the assay can also be used without any changes to provide reliable qualitative results. A review of data revealed that in the rare event of a less efficient PCR the sensitivity of 15 IU/mL is not guaranteed by the quantitative test with its current data analysis settings. An example of a PCR reaction which is inhibited but shows a valid QS result and a failed detection of target (2183 IU/mL) is given below:

An inhibited PCR reaction which yielded a valid result due to a valid QS and a result of "Target not detected" is shown in FIG. 4a. The QS was valid because it exceeded the fluorescence threshold settings which corresponded to 0.8 relative fluorescence units.

Figure 4B:
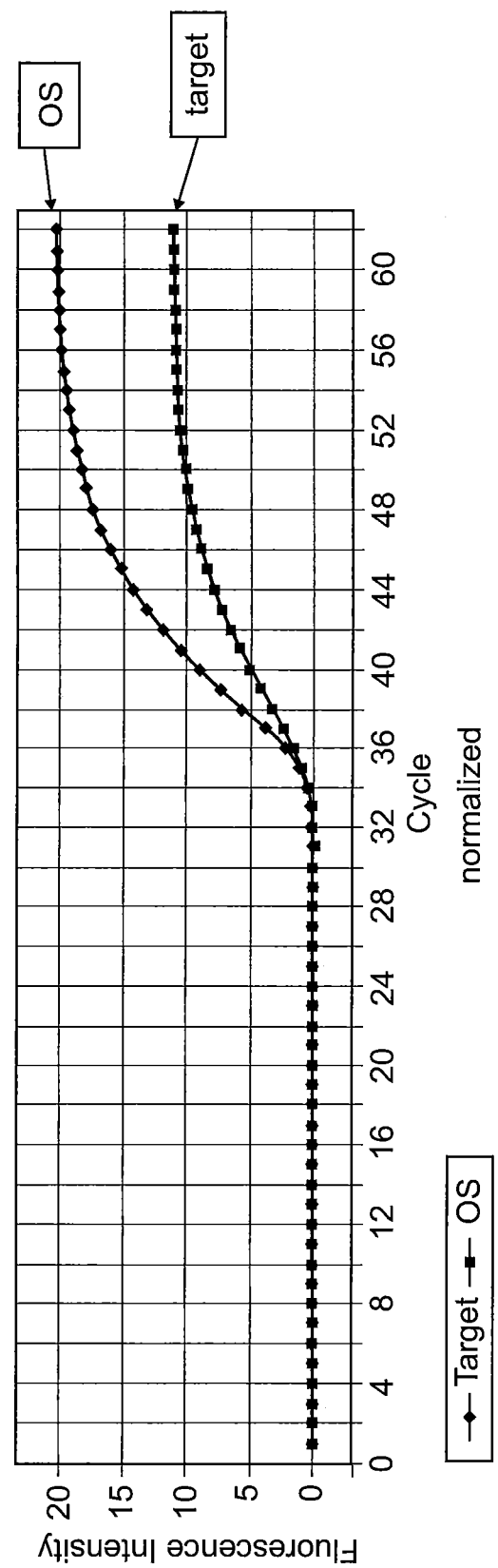

The repeat testing of the same sample showed a standard PCR reaction and a HCV titer result of 2183 IU/mL (FIG. 4b).

Thus the quantitative COBAS AmpliPrep/COBAS TaqMan HCV test without any changes cannot be used as qualitative test.

Using the above mentioned test the data analysis parameters settings of the IC/QS control nucleic acid were optimized such that a reliable qualitative result output is achieved. In order to demonstrate the general applicability, the optimization was additionally undertaken for all three commercial HBV, HCV and HIV-1 assays on the COBAS AmpliPrep/COBAS TaqMan system. By significantly raising the minimal relative fluorescence intensity (RFImin) threshold in the parameter settings the sensitivity of all three quantitative tests is ensured such that they can be used to provide a reliable qualitative result output. The relevant parameter settings are shown in Table 1 below:

TABLE 1

RFImin settings for the internal control of three COBAS AmpliPrep/COBAS TaqMan tests in the commercially available quantitative application and in a qualitative application.

|  | Quantitative RFImin IQS | Qualitative RFImin IQS |
| --- | --- | --- |
| HBV test on the COBAS AmpliPrep/COBAS Taqman | 1.5 | 10.4 |
| HCV test on the COBAS AmpliPrep/COBAS Taqman | 1.8 | 9.0 |
| HIV-1 test on the COBAS AmpliPrep/COBAS Taqman | 1.2 | 20.4 |

The qualitative RFImin settings of 9.0 would invalidate the inhibited PCR reaction in the example given for HCV above.

The above RFImin settings for the qualitative result output cannot be used simultaneously for the quantitative result output because the presence of target may affect the fluorescence intensity of the IC/QS growth curves as shown in FIG. 1a. As a result the qualitative RFImin settings lead to a high percentage of IC/QS invalid reactions in the presence of high target concentrations. In contrast, this does not affect the validity of the qualitative result output as the IC must not be valid in the presence of target. The validity of the quantitative reaction is significantly affected, though.

Thus, if the same test reagents with one IC/QS are to be used to provide both a reliable qualitative result output with guaranteed sensitivity of the test and a reliable quantitative test result with acceptably low levels of QS invalid results this can only be achieved by analyzing the raw data with two different sets of parameter settings as suggested here.

Example 2

Figure 2:
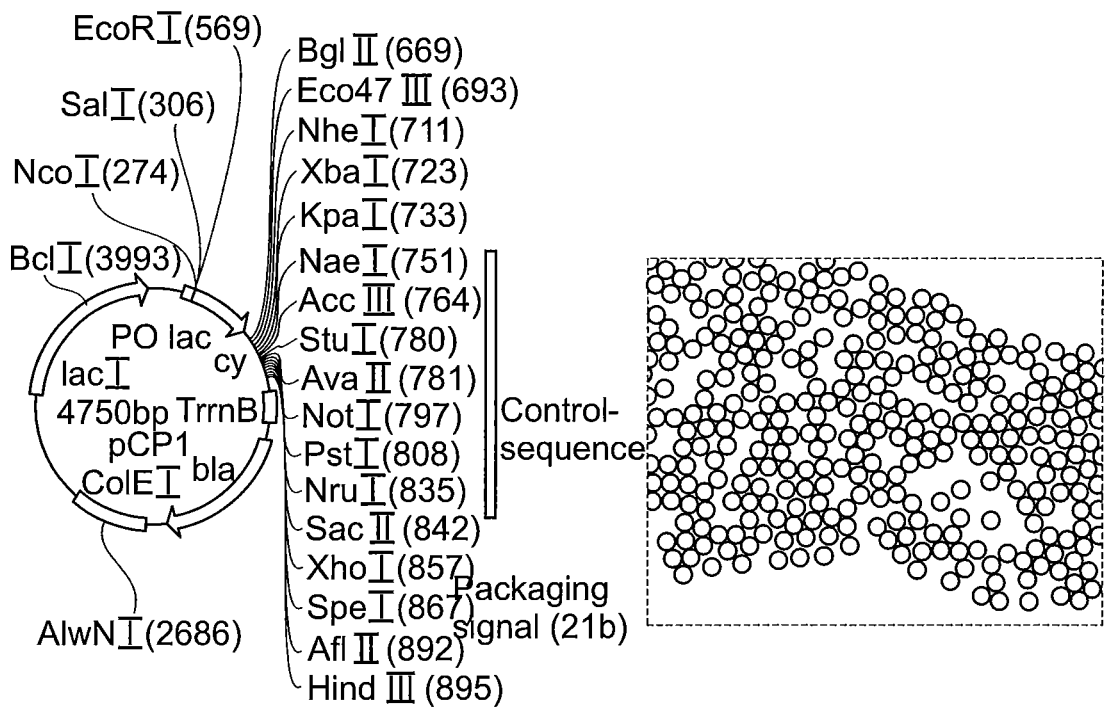
Figure 3:
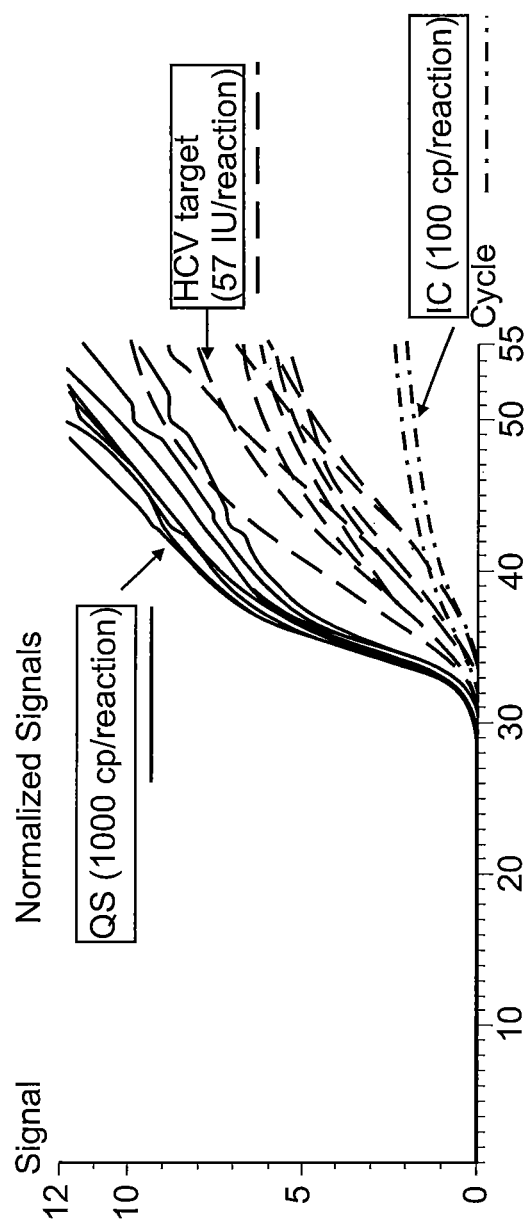

A First and a Second Control Nucleic Acid in Different Concentrations are Used for Obtaining a Quantitative and a Qualitative Result Output with the Same Test Reagents The goal is to provide both a reliable qualitative result output and a reliable quantitative test result with the same set of test reagents. In this approach to address this goal the internal control nucleic acid containing reagent comprises a formulation with two different armored RNA particles. The following reagents can be used for this experiment:

a) Sample preparation reagents of the COBAS AmpliPrep/COBAS TaqMan HCV test (magnetic particle suspension; protease solution, lysis buffer; elution buffer)
b) QS armored particle at a concentration level of about 1000 copies/reaction and an IC armored particle at a concentration level of about 100 copies/reaction. The production of armored RNA particles is shown in FIG. 2 below. The transcripts enclosed by the armored particles have different primer binding sites and different probe binding sites. The probes are labelled with the fluorescent labels HEX and CY5 together with the black hole quencher BHQ.

c) Magnesium reagent
d) Mastermix reagent comprising:
Z05 DNA polymerase and UNG
three different primer pairs for the target HCV, for the first and for the second control nucleic acid,
three different probes for the target labeled with FAM and BHQ, for the first control nucleic acid labeled with HEX and BHQ and for the second control nucleic acid labeled with CY5 and BHQ
Aptamer
dNTPs (dUTP, dATP, dCTP, dGTP, dTTP)
mastermix buffer ingredients (potassium acetate, glycerol, Tricine, DMSO, Betaine, IGEPAL, water), The sample preparation and the amplification/detection steps are performed using the specimen extraction parameters and the PCR file established for the COBAS AmpliPrep/COBAS TaqMan HCV Test. Growth curves for the three different fluorescent dyes are obtained and are presented in FIG. 3.

For the HCV samples the titers are determined as follows to obtain the quantitative result output: after a PCR run is complete, the fluorescence readings are processed to yield one set of dye concentration data for the QS nucleic acid (HEX fluorescent label), one set of dye concentration data for the qualitative standard nucleic acid (CY5 fluorescent label), and one set of dye concentration data for the target nucleic acid (FAM fluorescent label). All three sets of dye concentration data are processed in the same manner. The elbow values (CT) are calculated for the quantitative and the qualitative standard nucleic acid as well as the target nucleic acid. The elbow value is defined as the point where the fluorescence of the target nucleic acid or the two internal control nucleic acids crosses a predefined threshold (fluorescence concentration).

For the quantitative result output titer determination is done by analyzing only the dye concentration data for HEX and FAM. Titer determination is based on the assumption that the target nucleic acid and the QS nucleic acid are amplified with the same efficiency and that at the calculated elbow value equal amounts of amplicon copies of target nucleic acid and QS nucleic acid are amplified and detected. Therefore, the (CTQS−CTtarget) is linear to log (target conc/QS conc). The titer T can then be calculated for instance by using a polynomial calibration formula as in the following equation in which the only variable in the equation is the difference (CTQS−CTtarget):

$$T'=10(a(CTQS-CTtarget)2+b(CTQS-CTtarget)+c)$$

For the qualitative result output only the dye concentration data for CY5 and FAM are analyzed. By comparing the dye concentration data for CY5 and FAM the software determines whether the PCR reaction is target negative or positive. If the PCR reaction is target positive the IC result is neglected and thus may be valid or invalid. If the PCR reaction is target negative, the result is only valid if the IC shows a valid result. In the example shown above, all reactions contain low levels of HCV target and—although not relevant for the validity of the respective test results—all reactions show a valid IC.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

What is claimed is:

1. A method for simultaneously detecting and quantifying a microbial nucleic acid in a biological sample, the method comprising:
   a) providing a reaction mixture comprising:
      a control nucleic acid,
      one or more primer pairs that hybridize to distinct sequence portions of the microbial nucleic acid and to distinct sequence portions of the control nucleic acid, and
      two or more probes that hybridize to each of the sequences amplified by the one or more primer pairs, wherein the microbial nucleic acid and the control nucleic acid hybridize to different probes;
   b) adding the biological sample to the reaction mixture;
   c) performing one or more cycling steps, wherein each cycling step comprises:
      an amplifying step comprising producing one or more amplification products derived from the microbial nucleic acid if present in the sample and producing an amplification product derived from the control nucleic acid, and
      a hybridizing step comprising hybridizing the amplification products with the two or more probes, wherein the two or more probes are each labeled with a donor fluorescent moiety and a corresponding acceptor fluorescent moiety and each of the two or more probes carries a different fluorescent moiety dye; and
   d) qualitatively detecting and quantitatively measuring fluorescent signals generated in step c),
      wherein the fluorescent signals generated by the control nucleic acid and the microbial nucleic acid are proportional to their concentration and are indicative of the detection and quantification of the microbial nucleic acid,
      wherein the fluorescent signal from the control nucleic acid is indicative of an amplification occurring in the amplifying step even in the absence of the fluorescent signals from the microbial nucleic acid and
      wherein the fluorescent signal from the control nucleic acid is analyzed at a first fluorescence threshold to obtain a quantitative result and at a second fluorescence threshold to obtain qualitative result; thereby simultaneously detecting and quantifying the microbial nucleic acid in the biological sample.

2. A method for simultaneously detecting and quantifying a microbial nucleic acid in a biological sample, said method comprising:
   a) providing a reaction mixture comprising:
      a first and a second control nucleic acid in different concentrations, one or more primer pairs that hybridize to distinct sequence portions of the microbial nucleic acid and to distinct sequence portions of the first and the second control nucleic acid, and
      three or more probes that hybridize to each of the sequences amplified by the one or more primer pairs, wherein the microbial nucleic acid and the first and second control nucleic acid each hybridize to different probes;
   b) adding the biological sample to the reaction mixture;
   c) performing one or more cycling steps, wherein each cycling step comprises:
      an amplifying step comprising producing one or more amplification products derived from the microbial nucleic acid if present in the sample and producing an amplification product derived from the first control nucleic acid and an amplification product derived from the second control nucleic acid, and a hybridizing step comprising hybridizing the amplification products with the three or more probes, wherein the three or more probes are each labeled with a donor fluorescent moiety and a corresponding acceptor fluorescent moiety and each of the three or more probes carries a different fluorescent moiety dye; and d) qualitatively detecting and quantitatively measuring fluorescent signals generated in step c), wherein the fluorescent signals generated by the first control nucleic acid and the microbial nucleic acid are proportional to their concentration and are indicative of the detection and quantification of the microbial nucleic acid, wherein the fluorescent signal from the second control nucleic acid is indicative of an amplification occurring in the amplifying step even in the absence of the fluorescent signals from the microbial nucleic acid and wherein a first fluorescent signal from the first control nucleic acid is analyzed to obtain a quantitative result and a second fluorescent signal from the second control nucleic acid is analyzed to obtain a qualitative result;

thereby simultaneously detecting and quantifying a microbial nucleic acid in a biological sample.

3. The method of claim 2, wherein the first control nucleic acid is a quantitative standard nucleic acid and the second control nucleic acid is a qualitative internal control nucleic acid.

4. The method of claim 1, wherein the amplifying step employs a polymerase enzyme having 5' to 3' exonuclease activity.

5. The method of claim 2, wherein the first control nucleic acid is present in a concentration of 20-5000 times the limit of detection of the microbial nucleic acid, and wherein the second control nucleic acid is present in a concentration of 1-25 times the limit of detection of the microbial nucleic acid.

6. The method of claim 2, wherein the first and the second control nucleic acid are provided within one control reagent.

7. The method of claim 1, further comprising: in step d) determining the quantity of the microbial nucleic acid in the biological sample by comparison of the fluorescent signals generated by the microbial nucleic acid and the control nucleic acid.

8. The method of claim 1, further comprising: in step d) detecting the microbial nucleic acid in the biological sample by comparison of the fluorescent signals generated by the microbial nucleic acid and the control nucleic acid.

9. The method of claim 2, further comprising: in step d) determining the quantity of the microbial nucleic acid in the biological sample by comparison of the fluorescent signals generated by the microbial nucleic acid and the first control nucleic acid.

10. The method of claim 2, further comprising: in step d) detecting the microbial nucleic acid in the biological sample by comparison of the fluorescent signals generated by the microbial nucleic acid and the second control nucleic acid.

11. The method of claim 1, wherein the second fluorescence threshold is higher than the first fluorescence threshold.

* * * * *

UNITED STATES PATENT AND TRADEMARK OFFICE
CERTIFICATE OF CORRECTION

PATENT NO.        : 8,877,464 B2
APPLICATION NO.   : 13/191700
DATED             : November 4, 2014
INVENTOR(S)       : Babiel et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 129 days.

Signed and Sealed this
Sixth Day of June, 2017

Michelle K. Lee
*Director of the United States Patent and Trademark Office*